United States Patent
Ilan et al.

(10) Patent No.: US 10,849,605 B2
(45) Date of Patent: Dec. 1, 2020

(54) DEVICE AND METHOD FOR THE APPLICATION OF A CURABLE FLUID COMPOSITION TO A PORTION OF A BODILY ORGAN

(71) Applicant: Omrix Biopharmaceuticals Ltd., Rehovot (IL)

(72) Inventors: Erez Ilan, Kibbutz Netzer Sereni (IL); Yotam Gurman, Kibbutz or Haner (IL); Moti Meron, Herzliah (IL)

(73) Assignee: Omrix Biopharmaceuticals, Ltd., Rehovot (IL)

( * ) Notice: Subject to any disclaimer, the term of this patent is extended or adjusted under 35 U.S.C. 154(b) by 193 days.

(21) Appl. No.: 14/134,124

(22) Filed: Dec. 19, 2013

(65) Prior Publication Data

US 2014/0188141 A1    Jul. 3, 2014

Related U.S. Application Data

(60) Provisional application No. 61/748,877, filed on Jan. 4, 2013.

(30) Foreign Application Priority Data

Dec. 30, 2012    (IL) ............................................. 223997

(51) Int. Cl.
*A61B 17/00* (2006.01)
*A61H 33/00* (2006.01)
(Continued)

(52) U.S. Cl.
CPC ....... *A61B 17/00491* (2013.01); *A61H 33/00* (2013.01); *A61B 17/11* (2013.01);
(Continued)

(58) Field of Classification Search
CPC ............ A61B 2017/1107; A61B 17/11; A61B 2017/1139; A61B 17/00491;
(Continued)

(56) References Cited

U.S. PATENT DOCUMENTS

| 3,786,817 A | 1/1974 | Palma |
| 5,141,516 A | 8/1992 | Detweiler |

(Continued)

FOREIGN PATENT DOCUMENTS

| DE | 4315812 | 12/1994 |
| GB | 2133283 | 7/1984 |

(Continued)

OTHER PUBLICATIONS

Ho, Y-H. et al. "Techniques for Colorectal Anastomosis", World J. Gastroenterol. (2010) 16 (13) pp. 1610-1621.

(Continued)

*Primary Examiner* — Todd J Scherbel
*Assistant Examiner* — Mikail A Mannan
(74) *Attorney, Agent, or Firm* — David R. Crichton

(57) ABSTRACT

Disclosed are devices and methods suitable for application of a curable fluid composition to a bodily organ, such as to a lower portion of a bodily organ. The device comprises a monolithic piece of material having a lower surface, two spaced-apart sides, and two spaced-apart walls connecting the two spaced-apart sides. A receptacle for containing the curable fluid composition is defined by the lower surface, the two sides, and the two walls. At least a portion of the height of the two walls is less than the height of at least a portion of the two sides. The device is deployable underneath the bodily organ such that a lower portion of the bodily organ is supported by at least a portion of each of the two walls.

8 Claims, 2 Drawing Sheets

(51) Int. Cl.
  *A61H 35/00*   (2006.01)
  *A61B 50/30*   (2016.01)
  *A61B 90/40*   (2016.01)
  *A61B 90/60*   (2016.01)
  *A61B 17/11*   (2006.01)

(52) U.S. Cl.
  CPC ............... *A61B 90/40* (2016.02); *A61B 90/60* (2016.02); *A61B 2050/3014* (2016.02); *A61H 33/6005* (2013.01); *A61H 35/00* (2013.01); *A61H 2205/06* (2013.01); *A61H 2205/106* (2013.01); *A61H 2205/108* (2013.01)

(58) Field of Classification Search
  CPC .... A61B 2019/0285; A61B 2019/0212; A61B 2017/1103; A61B 2017/1121; A61B 2017/1132; A61B 2017/1135; A61B 2017/1225; A61B 17/08; A61B 17/081; A61B 17/083; A61B 17/085; A61B 17/1128; A61B 17/1114; A61B 17/0487; A61B 17/122; A61B 17/1222; A61B 17/128; A61B 17/1285; A61B 2017/1114; A61B 2017/1125; A61F 2/064; A61F 5/0086; A61H 35/00; A61H 33/6005; B65D 33/16; A61M 25/02–04
  USPC ........................................................ 606/153
  See application file for complete search history.

(56) References Cited

U.S. PATENT DOCUMENTS

| | | | |
|---|---|---|---|
| 5,381,562 A * | 1/1995 | Holloway et al. ................. | 4/516 |
| 5,447,504 A | 9/1995 | Baker et al. | |
| 5,792,835 A | 8/1998 | Tse et al. | |
| 5,972,371 A | 10/1999 | Gilchrist et al. | |
| 6,121,232 A | 9/2000 | Nur et al. | |
| 7,125,569 B2 | 10/2006 | Nur et al. | |
| 7,530,484 B1 * | 5/2009 | Durrani .............. | A61B 17/0682 227/109 |
| 7,972,357 B2 | 7/2011 | Bettuchi | |
| 2004/0052768 A1 | 3/2004 | Morrison et al. | |
| 2004/0059378 A1 * | 3/2004 | Peterson ............... | A61B 17/064 606/219 |
| 2010/0121278 A1 | 5/2010 | Fowler | |
| 2011/0238097 A1 | 9/2011 | Bettuchi | |
| 2011/0264122 A1 | 10/2011 | Bonino et al. | |
| 2013/0068815 A1 * | 3/2013 | Bruewer ............. | A61B 17/0644 227/175.1 |
| 2013/0331839 A1 * | 12/2013 | Hester ................ | A61B 17/0642 606/75 |

FOREIGN PATENT DOCUMENTS

| | | |
|---|---|---|
| JP | 2008-516697 | 5/2008 |
| JP | 2011-092347 | 5/2011 |
| WO | WO 93/05822 | 4/1993 |
| WO | WO 98/33533 | 8/1998 |
| WO | WO 02095019 | 11/2002 |
| WO | WO 2007/030892 | 3/2007 |
| WO | WO 2007/059801 | 5/2007 |

OTHER PUBLICATIONS

Vilela et al 'What is important for a continent catheterizable stomas: Angulations or Extension?' Int. Braz J Urol (2007) vol. 33(2) pp. 254-263.

International Preliminary Report re: PCT/IL2013/000097 dated Jul. 9, 2015.

International Search Report re: PCT/IL2013/000097 dated Apr. 7, 2014.

Search Report issued by State Intellectual Property Office of People's Republic China re: 201380068970.9 dated Nov. 4, 2016.

Chekan, E. et al 'Surgical stapling device-tissue interactions: what surgeons need to know to improve patient outcomes' Medical Devices: Evidence and Research (2014) pp. 305-318.

Hanna, K., et al 'Shorter circular staple is height associated with lower anastomotic stricture rate in laparoscopic gastric bypass' Surgery for Obesity and Related Diseases (2012) pp. 181-184.

* cited by examiner

DEVICE AND METHOD FOR THE APPLICATION OF A CURABLE FLUID COMPOSITION TO A PORTION OF A BODILY ORGAN

FIELD OF THE INVENTION

The invention relates to the field of devices for application of a curable fluid composition to a bodily organ, and more particularly, to a device for applying a curable fluid composition to a lower portion of a bodily organ, and methods of use thereof.

BACKGROUND OF THE INVENTION

Application of sealant, such as fibrin sealant, is useful for preventing leakage of fluids, such as air and/or liquid from tissues. In surgical procedures, fibrin sealant may be applied to wounds, including bleeding or non-bleeding wounds e.g. by dripping or spraying the sealant onto the wound. For example, fibrin sealant is commonly used during an anastomosis procedure, wherein the organ is sutured or stapled around the entire incision line and fibrin sealant is applied along the staple or suture line for reinforcement and to prevent leakage.

Fibrin sealant is typically a blood product obtained from either commercial sources or some regional blood transfusion centers. Components that are commonly used in the preparation of fibrin sealants are predominantly a fibrinogen component [which can optionally be supplemented with various quantities of Factor VIII, Factor XIII, fibronectin, vitronectin and von Willebrand factor (vWF)] and a thrombin component (which is typically supplemented with calcium). The fibrinogen component is typically activated by the thrombin component which is the last protease of the coagulation cascade.

Fibrin sealant is formed by an enzymatic reaction involving inter alia, fibrinogen, thrombin and Factor XIII. The thrombin converts the fibrinogen to fibrin by enzymatic action at a rate determined by the concentration of thrombin. Factor XIII, is typically present in the fibrinogen component of the sealant and is an enzyme of the blood coagulation system that cross-links and stabilizes the fibrin clot. This process bypasses most of the steps of normal coagulation and mimics its last phase. Some manufacturers add antiproteolytic agents to the fibrin sealant formulation (as described in WO 93/05822) or specifically remove the plasminogen in order to stop or delay the fibrinolysis (as described in U.S. Pat. Nos. 5,792,835 and 7,125,569).

Fibrin sealant is commonly applied by spraying the fibrinogen component and the thrombin component by air assisted spraying, airless spray, or by dripping application.

Application of fibrin to a lower portion of a bodily organ by spraying or dripping is problematic since complete coverage around the organ is very difficult to achieve due to inaccessibility of at least a part of the organ within the body e.g. the lower part of the organ. In dripping application of fibrin sealant, gravity pulls the drop downwards such that the drop does not remain in a desired target location and a large portion of the applied composition drips off the organ.

To overcome the above problems, surgeons may flip or twist the organ in order to apply fibrin sealant onto the lower surface of the organ. However, aggressive/rough handling of the organ may result in leakage from the organ e.g. leakage from the suture/staple line of an anastomized organ. Also, when the space around the organ is limited it is not possible to flip the organ.

Moreover, in situations when access to the area is difficult e.g. narrow regions, and spraying is used as the application method, an angular and long tip is required to reach the target area and thus the edge of the tip may be positioned too close to the tissue surface such that adequate spraying is not attainable. Also, spraying from close proximity to the target is challenging due to effect of air on pre-cured fibrin which yields regions which are uncovered with fibrin at the target place.

Due to the above challenges and difficulties, a surgeon may not be able to easily create a continuous layer of sealant at the lower portion of a bodily organ, such as a cylindrical and/or hollow organ, by using the conventional methods e.g. spraying and dripping.

Background art includes US 2011/0238097; US 2004/052768; U.S. Pat. No. 5,972,371; 5,141,516; 7,972,357; US 2010/121278; US 2011/264122; WO 2007/030892; and U.S. Pat. No. 3,786,817.

SUMMARY OF THE INVENTION

The invention, in some embodiments thereof, relates to a device for applying a curable fluid composition to a lower portion of a bodily organ, and methods of use thereof.

Aspects and embodiments of the invention are described in the specification hereinbelow and in the appended claims.

According to an aspect of some embodiments of the invention, there is provided a device suitable for application of a curable fluid composition to a bodily organ, the device comprising: a monolithic piece of material having a lower surface, two spaced-apart sides, and two spaced-apart walls connecting the two spaced-apart sides, wherein at least a portion of the height of the two spaced-apart walls is less than the height of at least a portion of the two spaced-apart sides, wherein a receptacle for containing the curable fluid composition therein is defined by the lower surface, the two spaced-apart sides, and the two spaced-apart walls, the device deployable underneath the bodily organ such that a tower portion of the bodily organ is supported by at least a portion of each of the two spaced-apart walls.

In some embodiments, the device disclosed herein is for application of the curable fluid composition onto a defect in the bodily organ, such as, for example, a defect formed following anastomosis.

In some embodiments of the device disclosed herein, at least a first portion of each of the two spaced-apart watts, proximal to at least one of the two spaced-apart sides of the device, has a height greater than that of a second portion of each of the two spaced-apart walls, wherein when the device is deployed underneath the bodily organ such that the lower portion of the bodily organ is supported by the second portion of each of the two spaced-apart walls, at least one gap is created between a side of the bodily organ and the at least one side of the device.

In some embodiments, the portion of each of the two spaced-apart walls, proximal to each of the two spaced-apart sides, has a height greater than that of the second portion of each of the two spaced-apart walls, wherein when the device is deployed underneath the bodily organ such that the lower portion of the bodily organ is supported by the second portion of each of the two spaced-apart walls, a gap is created between each side of the bodily organ and each side of the device.

In some embodiments, the device is made of a rigid or semi-rigid material, such as, for example, a material selected from the group consisting of silicone rubber, nylon, polyurethane, polyester, polytetrafluoromethylene (PTFE), polychloroprene, or a combination thereof.

In some embodiments, each of the two spaced-apart sides has a length in the range of from about 1 to about 6 cm. In some embodiments, each of the two spaced-apart walls has a length in the range of from about 2 to about 10 cm.

In some embodiments, each of the two spaced-apart sides has a height in the range of from about 5 to about 70 mm. In some embodiments, at least a portion of each of the two spaced-apart walls has a height in the range of from about 2 to about 15 mm.

In some embodiments, each of the two spaced-apart sides has a thickness in the range of from about 1 to about 15 mm. In some embodiments, each of the two spaced-apart walls has a thickness in the range of from about 1 to about 15 mm.

In some embodiments, the lower surface has a thickness in the range of from about 0.5 to about 10 mm.

According to an aspect of some embodiments of the invention, there is provided a method for applying a curable fluid composition to a bodily organ, the device comprising: providing a device according to any of the embodiments disclosed herein; deploying the device underneath the bodily organ such that the lower portion of the bodily organ is supported by at least a portion of each of the two spaced-apart walls; and introducing an amount of the curable fluid composition into the receptacle sufficient to contact at least a portion of the bodily organ located between the two spaced-apart sides, thereby applying the composition to the bodily organ.

In some embodiments, deploying the device underneath the bodily organ comprises lifting the bodily organ, placing the device beneath the bodily organ, and positioning the bodily organ between the two spaced-apart sides, wherein a lower portion of the bodily organ is supported by at least a portion of each of the two spaced-apart walls.

In some embodiments, introducing of the curable fluid composition into the receptacle is carried out through the at least one gap.

In some embodiments, the curable fluid composition is applied directly onto an upper portion of the bodily organ, so that at least a portion of the applied curable fluid composition contacts the upper portion of the bodily organ and flows down at least on one side of the bodily organ and into the receptacle through the at least one gap.

In some embodiments, a first portion of the applied composition remains on the at least upper portion and/or on the at least one side of the bodily organ, and a second portion of the applied composition flows downwards to the receptacle and thereby covers at least part of the lower portion of the bodily organ located between the two spaced-apart sides.

In some embodiments, the curable fluid composition is applied by spraying, dripping and/or pouring.

In some embodiments, the bodily organ is a hollow organ.

In some embodiments, the method disclosed herein is for repairing a defect in the bodily organ.

In some embodiments, the bodily organ is an anastomized bodily organ.

In some embodiments, the anastomsis is carried out by stitching or stapling.

In some embodiments, the bodily organ is selected from the group consisting of a rectum, and an anus.

In some embodiments, the curable fluid composition comprises at least two components. In some embodiments, a first of the at least two components is activated by a second of the at least two components. In some such embodiments, the first component comprises fibrinogen. In some such embodiments, the second component comprises thrombin.

In some embodiments, the method disclosed herein further comprises allowing the curable fluid composition to cure, such as, for example, for a time in the range of from about 5 seconds to about 5 minutes. In some embodiments, the method further comprises removing the device subsequent to curing of the curable fluid composition.

In some embodiments, the device and methods described herein addresses the challenges of accurately applying a continuous layer of a curable fluid composition, such as fibrin sealant, to a lower portion of a bodily organ, for example, an organ that is positioned in a narrow area which is difficult to access, such as the rectum.

In some embodiments, the device described herein has at least one of the following advantages: enables continuous and/or full coverage of a desired location on a bodily organ; application of curable fluid composition to the lower portion of the organ can be carried out with minimal handling of the organ (e.g. without the need of flipping/twisting the organ); a single device may be used with a range of bodily organs of different sizes, or at different locations on a non-uniform organ; enables accurate application of curable composition even on an area of a target organ which is difficult or impossible to access using other means; easy to use; deploying the device and optionally removing it after use can be carried out with minimal contact with the anastomized organ; cheap and simple to produce and is suitable for a single use; enables application of curable fluid composition against gravity; and prevents leakage of the applied fluid (prior to curing) by providing a volume for containing the fluid.

In some embodiments, wherein the device is devoid of an inlet and application of the curable fluid composition is carried out through a gap created between a side of the bodily organ and the side of the device, the risk of blockage of an inlet due to curing of the curable fluid composition is avoided, permitting use of a fast-curing composition, such as fibrin sealant with a thrombin component having a high thrombin concentration (e.g. a thrombin concentration in the range of from about 250 to about 1000 IU/ml).

The device and method described herein are particularly useful for accurate application of a sealant, such as a fibrin sealant, to a lower portion of a bodily organ e.g. onto a defect present beneath a bodily organ e.g. following anastomosis by suturing or stapling. The method described herein facilitates superior sealing and can be used to prevent leakage along the suture/staple line. In some embodiments, the device and method described herein enable a desired volume of sealant to be applied, resulting in formation of a continuous fibrin layer on the organ having a height. In some embodiments, the sealant is formed in situ upon curing of a curable fluid composition.

In some embodiments, the device described herein is deployable on a selected portion of an organ e.g. a defected region, enabling accurate application of a curable fluid composition onto a selected area.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate the numerical value +/−10%.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
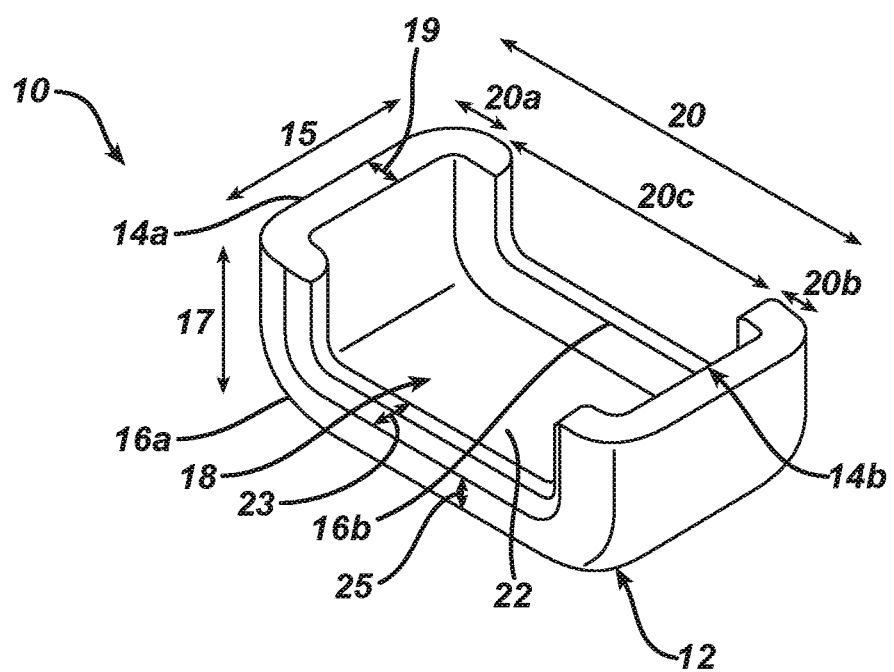
FIG. 1 is a perspective view of an embodiment of the device as described herein.

The invention, in some embodiments thereof, relates to a device for applying a curable fluid composition to a lower portion of a bodily organ, and methods of use thereof.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. The phraseology and terminology employed herein are for descriptive purpose and should not be regarded as limiting.

According to an aspect of some embodiments of the invention, there is provided a device [10] suitable for application of a curable fluid composition to a bodily organ [30], the device comprising: a monolithic piece of material having a lower surface [12], two spaced-apart sides [14a, 14b], and two spaced-apart walls [16a, 16b] connecting the two spaced-apart sides, wherein at least a portion [20c] of the height [25] of the two spaced-apart walls is less than the height [17] of at least a portion of the two spaced-apart sides, wherein a receptacle [18] for containing the curable fluid composition therein is defined by the lower surface, the two spaced-apart sides, and the two spaced-apart walls, the device deployable underneath the bodily organ such that a lower portion of the bodily organ is supported by at least a portion of each of the two spaced-apart walls.

In some embodiments, the device disclosed herein is for application of the curable fluid composition onto a defect in the bodily organ, such as, for example, a defect formed following anastomosis.

In some embodiments of the device disclosed herein, at least a first portion [20a, 20b] of each of the two spaced-apart walls, proximal to at least one of the two spaced-apart sides of the device, has a height greater than that of a second portion [20c] of each of the two spaced-apart walls, wherein when the device is deployed underneath the bodily organ such that the lower portion of the bodily organ is supported by the second portion of each of the two spaced-apart walls, at least one gap [32a, 32b] is created between a side of the bodily organ [34] and the at least one side of the device.

In some embodiments, the portion of each of the two spaced-apart walls, proximal to each of the two spaced-apart sides, has a height greater than that of the second portion of each of the two spaced-apart walls, wherein when the device is deployed underneath the bodily organ such that the lower portion of the bodily organ is supported by the second portion of each of the two spaced-apart walls, a gap is created between each side of the bodily organ and each side of the device.

In some embodiments, the device is made of a rigid or semi-rigid material, such as, for example, a material selected from the group consisting of silicone rubber, nylon, polyurethane, polyester, polytetrafluoromethylene (PTFE), polychloroprene, or a combination thereof.

In some embodiments, each of the two spaced-apart sides [14a, 14b] has a length [15] in the range of from about 1 to about 6 cm. In some embodiments, each of the two spaced-apart walls [16a, 16b] has a length [20] in the range of from about 2 to about 10 cm.

In some embodiments, each of the two spaced-apart sides [14a, 14b] has a height [17] in the range of from about 5 to about 70 mm. In some embodiments, at least a portion [20c] of each of the two spaced-apart walls [16a, 16b] has a height [25] in the range of from about 2 to about 15 mm.

In some embodiments, each of the two spaced-apart sides [14a, 14b] has a thickness [19] in the range of from about 1 to about 15 mm. In some embodiments, each of the two spaced-apart walls [16a, 16b] has a thickness [23] in the range of from about 1 to about 15 mm.

In some embodiments, the lower surface [12] has a thickness in the range of from about 0.5 to about 10 mm.

According to an aspect of some embodiments of the invention, there is provided a method for applying a curable fluid composition to a bodily organ [30], the device comprising: providing a device according to any of the embodiments disclosed herein; deploying the device underneath the bodily organ such that the lower portion of the bodily organ is supported by at least a portion of each of the two spaced-apart walls; and introducing an amount of the curable fluid composition into the receptacle sufficient to contact at least a portion of the bodily organ located between the two spaced-apart sides, thereby applying the composition to the bodily organ.

In some embodiments, deploying the device underneath the bodily organ comprises lifting the bodily organ, placing the device beneath the bodily organ, and positioning the bodily organ between the two spaced-apart sides, wherein a lower portion of the bodily organ is supported by at least a portion of each of the two spaced-apart walls.

In some embodiments, introducing of the curable fluid composition into the receptacle is carried out through the at least one gap.

In some embodiments, the curable fluid composition is applied directly onto an upper portion of the bodily organ, so that at least a portion of the applied curable fluid composition contacts the upper portion of the bodily organ and flows down at least on one side of the bodily organ and into the receptacle through the at least one gap.

In some embodiments, a first portion of the applied composition remains on the at least upper portion and/or on the at least one side of the bodily organ, and a second portion of the applied composition flows downwards to the receptacle and thereby covers at least part of the lower portion of the bodily organ located between the two spaced-apart sides.

In some embodiments, the curable fluid composition is applied by spraying, dripping and/or pouring.

In some embodiments, the method disclosed herein is for repairing a defect in the bodily organ.

In some embodiments, the bodily organ is a hollow organ. In some embodiments, the bodily organ is an anastomized bodily organ. In some embodiments, the anastomsis is carried out by stitching or stapling.

In some embodiments, the bodily organ is selected from the group consisting of a rectum, and an anus.

In some embodiments, the curable fluid composition comprises at least two components. In some embodiments, a first of the at least two components is activated by a second of the at least two components. In some such embodiments, the first component comprises fibrinogen. In some such embodiments, the second component comprises thrombin.

In some embodiments, the method disclosed herein further comprises allowing the curable fluid composition to cure, such as, for example, for a time in the range of from about 5 seconds to about 5 minutes. In some embodiments, the method further comprises removing the device subsequent to curing of the curable fluid composition.

Figure 2:
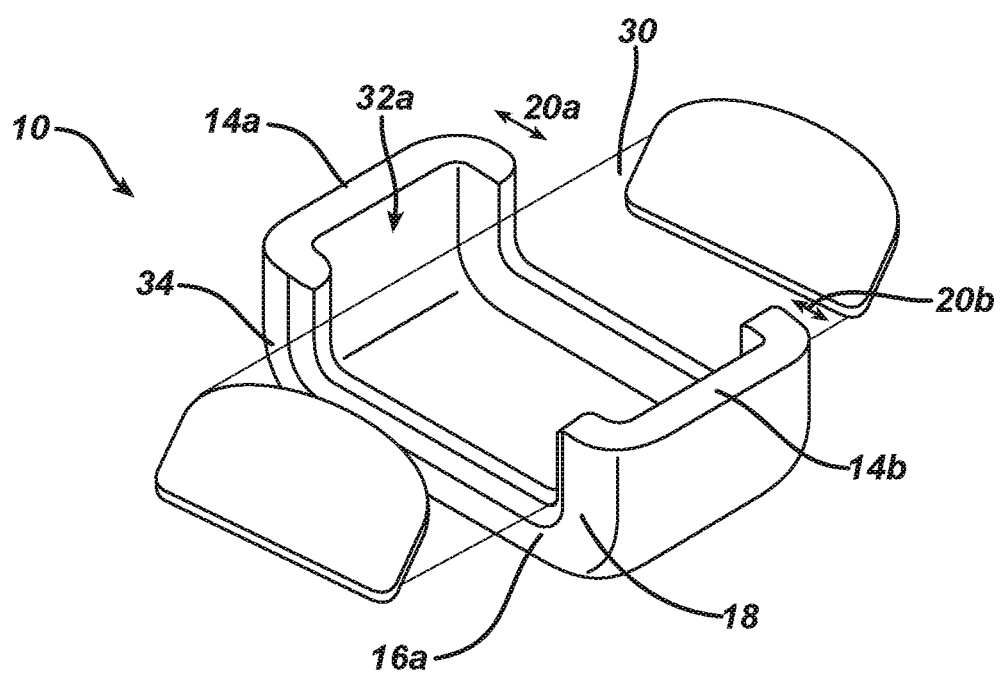
FIG. 2 is a perspective view of the device of claim 1, deployed underneath a bodily organ.

Referring now to FIG. 1, there is shown a perspective view of an exemplary embodiment of a device suitable for applying a curable fluid composition to a bodily organ (30, as shown in FIG. 2) e.g. to the lower portion of the organ. Device 10 comprises a monolithic piece of material having a lower surface 12, two spaced-apart sides 14a and 14b, and two spaced-apart walls 16a and 16b connecting spaced-apart sides 14a and 14b to each other. Spaced-apart sides 14a and 14b, spaced-apart walls 16a and 16b and lower surface 12 define a receptacle 18 having a void volume for containing the curable fluid composition. In some embodiment s of the invention, at least a portion of spaced-apart walls 16a and 16b are of equal height.

At least a portion of the height of spaced-apart walls 16a and 16b is less than that of spaced-apart sides 14a and 14b, forming a recessed area 22 along the length of spaced-apart walls 16a and 16b, such that when device 10 is deployed underneath bodily organ 30 (see FIG. 2), the lower portion of bodily organ 30 is supported by at least a portion of each of the two spaced-apart walls 16a and 16b, without contacting the upper face of lower surface 12, and sides 14a and 14b extend upwards at either side of bodily organ 30, to a height which is equal to or greater than the height of bodily organ 30 when positioned within device 10.

In the embodiment of FIG. 1, the height of portions 20a and 20b of the length of each of the two spaced-apart walls 16a and 16b, proximal to each of spaced-apart sides 14a and 14b, is greater than that of portion 20c of the length of each of the two spaced-apart walls 16a and 16b, such that a recessed portion 22 is formed along portion 20c.

As shown in FIG. 2, in some embodiments, when device 10 is deployed underneath bodily organ 30, gaps 32a and 32b (not shown) are defined between each side of bodily organ 30 and between spaced-apart sides 14a and 14b. In some embodiments, recessed portion 22 is U-shaped.

Alternatively, in some embodiments (not shown), the heights of portions 20a and 20c may be equal, and the height of 20b is greater, such that one edge of recess 22 is defined by side 14b, such that when device 10 is deployed underneath a bodily organ, a gap is defined between the side of the bodily organ proximal to side 14a of device 10 and between side 14a.

Further alternatively, in some embodiments, the heights of portions 20b and 20c may be equal, and the height of 20a is greater, such that one edge of recess 22 is defined by side 14a, such that when device 10 is deployed underneath a bodily organ, a gap is defined between the side of the bodily organ proximal to side 14b of device 10 and between side 14b.

In some embodiments, the device is made of a rigid or semi-rigid material. The rigid or semi-rigid material may comprise, for example, at least one of silicone rubber, nylon, polyurethane, polyester, polychloroprene, polytetrafluoroethylene (PTFE), or a combination thereof.

In some embodiments, the height and length of spaced-apart sides 14a and 14b and of each of spaced-apart walls 16a and 16b is selected such that the void volume of receptacle 18 can receive a desired volume of curable fluid composition and provide a continuous fibrin layer seal of a desired thickness, width and length.

In some embodiments, each of spaced-apart sides 14a and 14b has a length 15 in the range of from about 1 to about 6 cm. In some embodiments, each of spaced-apart sides 14a and 14b has a height 17 in the range of from about 5 to about 70 mm. In some embodiments, each of spaced-apart sides 14a and 14b has a thickness 19 in the range of from about 1 to about 15 mm.

In some embodiments, each of spaced-apart walls 16a and 16b has a length 20 in the range of from about 2 to about 10 cm. In some embodiments, at least a portion of each of spaced-apart walls 16a and 16b has a height that is equal to the height 17 of spaced-apart sides 14a and 14b e.g. in the range of from about 5 to about 70 mm. In some embodiments, at least a portion of each of spaced-apart walls 16a and 16b has a height 25 in the range of from about 2 to about 15 mm. In some embodiments, each of spaced-apart walls 16a and 16b has a thickness 23 in the range of from about 1 to about 15 mm. Heights of spaced-apart sides 14a and 14b and of spaced apart walls 16a and 16b are measured from the upper face of lower surface 12.

When device 10 is deployed underneath a bodily organ 30, as shown FIG. 2, such as by lifting bodily organ 30 and placing device 10 beneath bodily organ 30, spaced-apart sides 14a and 14b are arranged on either side of bodily organ 30, such that bodily organ 30 is supported by the shorter portion 20c of each of spaced-apart walls 16a and 16b, such that gaps 32a and 32b (not shown) are constituted between an outer surface 34 of each side of organ 30, and the inner surface of each of spaced-apart sides 14a and 14b.

In some embodiments, once device 10 is deployed beneath bodily organ 30, the curable fluid composition is introduced into receptacle 18 in an amount sufficient to contact at least a portion of the bodily organ located between the two spaced-apart sides 14a and 14b. In some embodiments, the amount of curable fluid composition introduced into receptacle 18 is sufficient to substantially fill the void volume of receptacle 18.

In some embodiments, the curable fluid composition is introduced into receptacle 18 through at least one gap 32a or 32b. In some embodiments, the curable fluid composition contacts an external surface of bodily organ 30 and flows down at least one side of bodily organ 30 through at least one of gaps 32*a* and 32*b*. In some such embodiments, the curable fluid composition is applied directly onto an upper portion of bodily organ 30, such as, for example, by spraying, dripping or pouring, wherein the curable fluid composition contacts the upper portion of bodily organ 30 and flows down at least one side of bodily organ 30, through at least one of gaps 32*a* and 32*b*, and accumulates in receptacle 18, contacting at least a portion of the lower portion of bodily organ 30 located between spaced-apart sides 14*a* and 14*b*. Alternatively, the curable fluid may be directly inserted through gaps 32*a* and 32*b* to accumulate in receptacle 18.

In some embodiments, at least a portion of the curable fluid composition remains on at least one side of bodily organ 30.

In some embodiments, additional curable fluid composition may further be applied to the upper portion of bodily organ 30 e.g. by dripping, spraying and/or pouring, in order to provide a fibrin seal around the entire organ e.g. along a suture/staple line of an anastomized organ. In some embodiments, the anastomized organ is a hollow organ.

In some embodiments (not shown), a device as described herein further comprises at least one inlet, defining a passage through the material e.g. a rigid or semi-rigid material for introducing the curable fluid composition into the receptacle.

Device 10 can be delivered to the desired location by any suitable means including, but not limited to, open surgery, and minimally invasive procedures (MIS) such as laparoscopy. In one embodiment of the invention, an incision is made proximal to bodily organ 30, and device 10 is deployed beneath bodily organ 30 via the incision. The patient can receive local, regional or general anesthesia.

The term "open surgery" refers to surgery wherein the surgeon gains direct access to the target organ via a relatively large incision. As used herein the term "minimally invasive procedure" means a procedure wherein the surgeon gains access to the target organ via small incisions or through a body cavity or anatomical opening e.g. via laparoscopy.

Embodiments of the device 10 described herein may be used to apply a curable fluid composition to a lower portion and optionally also to an upper portion of any bodily organ 30. For example, bodily organ 30 may be a blood vessel (including an artery, such as an aorta, or a vein, such as arena cava); an organ of the digestive system, including an esophagus, a stomach or part thereof (such as a cardia, a fundus, a body, or a pylorus), a small intestine or part thereof, (such as a duodenum, a jejunum or an ileum), a large intestine or part thereof (such as a colon, a cecum, a rectum, or an anus), a bowel, or a pancreas; a dura; an organ of the respiratory system such as a trachea; or an organ of the urinary system (such as a ureter, a urethra, a kidney, or a urinary bladder).

Device 10 may be used to apply a curable substance to a lower portion of a surface of a bodily organ 30 of a patient. The term "a surface of a body part of a patient" refers to an external surface of the body that can be seen by unaided vision and to a surface of an internal body part which is a part of the internal anatomy of an organism. The surface can be a bleeding or a non-bleeding site.

Device 10 can be used for applying a curable substance to a lower portion of a bodily organ 30 in order to decrease the risk of postoperative adhesion formation.

The term "adhesion" refers to an abnormal attachment between tissues and/or organs. Typically, adhesions occur after surgical procedures such as following rough manipulation of tissues; following tissue surface drying; and/or due to the presence of reactive foreign bodies (e.g. suture materials, talc powder or lint residues) in the operated area.

In some embodiments, device 10 is useful for application of a curable fluid composition on a defect in a bodily organ 30. Organ 30 may be an anastomized organ an organ that was subjected to an anastomosis surgical procedure), wherein anastomosis was achieved, for example, by stapling and/or suturing, and a curable fluid composition is applied onto the staple/suture line for reinforcement and/or to prevent leakage from the anastomized organ.

As used herein, the term "defect" refers to a tear, aperture, bore, fissure, puncture, hole, crack, opening, slit, gap, perforation, fracture, puncture or rupture, leak e.g. in a tissue. For example, the defect can be formed following an anastomosis procedure. The defect can be congenital e.g. hernia; a condition resulting from body related pathology e.g. seroma, hernia, infection, inflammation; formed after surgery, suturing and/or stapling; or a condition resulting from a non body factor e.g. accidents, injuries.

The curable fluid composition according to the invention can be applied onto at least a part of the bodily organ such as a staple/suture line present beneath a bodily organ; for strongly affixing prosthesis e.g. during a hernia operation; for staple/suture line reinforcement; to prevent or diminish alveolar air leakage; treating or preventing renal defects; treating or preventing fistulas; treating or preventing heart defects e.g. penetrating heart wounds; reinforcing of a vascular graft prosthesis; and treating or preventing cerebrospinal fluid leakage.

As used herein, the term "anastomosis" typically refers to a surgical procedure which is used to reconnect two or more sections of an organ or tissue. The procedure can be used following sectioning of the urinary tract (urethra), throat (esophagus), or in bowel surgery. The procedure can also be used following the excision of a diseased tissue (such as inflamed, cancerous or otherwise pathological tissue e.g. ulcerative disease).

As used herein, the term "staple or suture" includes any fastener which is used for closing a wound such as, but not limited to, staple, clip, pin, hook, suture and the like.

As used herein, the terms "leak" and "leakage" refer to the escape or passage of a substance e.g. fluid, viscous material and/or air e.g. through a tear, aperture, bore, fissure, puncture, hole, crack, opening, slit, gap, perforation, fracture, puncture or rupture in a tissue.

In one embodiment of the invention, device 10 is used to apply a curable fluid composition to a lower and optionally also to an upper portion of a blood vessel for hemostasis.

As used herein, the term "hemostasis" refers to the ability of an agent to stop the bleeding from an injured blood vessel and/or to contribute to keeping the blood contained within the blood vessel.

In one embodiment of the invention, bodily organ 30 is a hollow organ.

In some embodiments, curable fluid compositions useful for application using embodiments of the device described herein comprise a composition which can undergo an interaction between its components leading to an increase in viscosity of the composition. Such interactions include polymerization and/or cross-linking of components, achieved by means that include, but are not limited to, use of activating agents such as catalysts, or physical activators such as heat, radiation e.g. ultraviolet radiation, electron beams, or combinations thereof.

As used herein, the term "fluid" refers to any biological fluid (e.g. fluid which derives from living organisms or which is manufactured by recombinant technology) and/or chemical fluid (e.g. fluid which is chemically synthesized).

In some embodiments, curing of the curable fluid composition occurs within a time range of from a few miliseconds to a few minutes, for example in the range of from 2 miliseconds to 10 minutes, or from about 5 seconds to about 5 minutes.

In some embodiments, the curable fluid composition comprises at least two components. In some embodiments comprising two components, a first of the two components is activated by a second of the two components. For example, the first component optionally comprises fibrinogen, and the second component optionally comprises an agent which activates fibrinogen, such as thrombin or a substance obtainable from snake venom, such that a fibrin polymer is formed upon curing of the curable fluid composition. Additional, non-limiting examples of two components of the curable fluid composition described herein include alginate and calcium; chondroitin sulphate and an acid such as hyaluronic acid.

For embodiments wherein the curable fluid composition comprises fibrinogen and thrombin components, one or both of the components can optionally be prepared from an initial blood composition. The blood composition can be whole blood or blood fractions, i.e. a fraction of whole blood such as plasma. The origin of the fibrinogen and thrombin can be autologous whereby they would be manufactured from the patient's own blood, from pooled blood or fractions. It is also possible that the protein components are prepared by recombinant methods.

In one embodiment of the invention, the fibrinogen component comprises a biologically active component (BAC) which is a solution of proteins derived from blood plasma, optionally further comprising anti fibrinolytic agents such as tranexamic acid and/or stabilizers such as arginine, lysine, pharmaceutically acceptable salts thereof, or mixtures thereof. BAC is optionally derived from cryoprecipitate, in particular concentrated cryoprecipitate.

The term "cryoprecipitate" refers to a blood component which is obtained from frozen plasma prepared from whole blood, recovered plasma or from source plasma which is collected by plasmapheresis. A cryoprecipitate is optionally obtained when frozen plasma is slowly thawed in the cold, typically at a temperature of 0-4° C., resulting in the formation of precipitate that contains fibrinogen and factor XIII. The precipitate can be collected, for example, by centrifugation and dissolved in a suitable buffer such as a buffer containing 120 mM sodium chloride, 10 mM trisodium citrate, 120 mM glycine, 95 mM arginine hydrochloride, 1 mM calcium chloride. The solution of BAC optionally comprises additional factors such as for example factor VIII, fibronectin, von Willebrand factor (vWF), vitronectin, etc. for example as described in U.S. Pat. No. 6,121,232 and WO9833533. The composition of BAC optionally comprises stabilizers such as tranexamic acid and arginine hydrochloride. The amount of tranexamic acid in the solution of BAC is optionally in the range of from about 80 to about 110 mg/ml. The amount of arginine hydrochloride is optionally in the range of from about 15 to about 25 mg/ml.

Optionally, the solution is buffered to a physiological compatible pH value. The buffer comprises glycine, sodium citrate, sodium chloride, calcium chloride and water for injection as a vehicle. Glycine is optionally present in the composition at a concentration in the range of from about 6 to about 10 mg/ml; sodium citrate is optionally present at a concentration in the range of about 1 to about 5 mg/ml; sodium chloride is optionally present at a concentration in the range of from about 5 to about 9 mg/ml; and calcium chloride is optionally present at a concentration in the range of from about 0.1 to about 0.2 mg/ml.

In one embodiment of the invention, the fibrinogen component is derived from blood e.g. BAC composition. In another embodiment of the invention, the concentration of plasminogen and/or plasmin in the blood derived component is lowered. The removal of plasmin and plasminogen from the blood derived component can be carried out as described in U.S. Pat. No. 7,125,569 and WO02095019.

The thrombin component optionally comprises human thrombin (800-1200 IU/ml), calcium chloride, human albumin, mannitol, sodium acetate and water for injection.

Components of a fibrin sealant comprising fibrinogen and thrombin are available from manufacturers such as OMRIX e.g. EVICEL®, QUIXIL®, ADHEXIL™; EVITHROM®; Baxter e.g. TISEEL®; CSL e.g. Beriplast® and the like.

In one embodiment, the fibrinogen and thrombin components are manufactured from pooled human source plasma and provided as a single use kit consisting of two vials: one vial contains a Biological Active Component 1 or 2 (BAC1 or BAC2) and another vial comprises the thrombin component.

In some embodiments, the concentration of the fibrinogen component is about 60 mg/ml, and the concentration of the thrombin component is about 1000 IU/ml.

The components of the fibrin sealant may be mixed in any desired range of ratios in the method of the invention. For example, when the concentration of fibrinogen in the fibrinogen component is 40-85 mg/ml and the thrombin concentration in the thrombin component is about 800-1200 IU/ml, the two components can be mixed in a ratio of 1:1, 2:1, 3:1, 4:1, 5:1, 6:1, 7:1, 8:1, 9:1, 10:1, 1:2, 1:3, 1:4, 1:5, 1:6, 1:7, 1:8, 1:9, 1:10, respectively, and so on.

In some embodiments, curable fluid compositions comprising at least two components may be introduced into receptacle 18 by introducing a first of the two components into a gap 32a on a first side of bodily organ 30 and introducing a second of the two components into a gap 32b on a second side of bodily organ 30. In some embodiments, curable fluid compositions comprising at least two components may be introduced into receptacle 18 by introducing a first of the two components into a gap 32b on a second side of bodily organ 30 and introducing a second of the two components into a gap 32a on a first side of bodily organ 30. The two components may be introduced substantially simultaneously, or sequentially. Alternatively, each of the two components may be introduced through the same gap 32a or 32b, either substantially simultaneously or sequentially. In one embodiment, the two components are both introduced substantially simultaneously through the same gap 32a or 32b.

In one embodiment of the invention, following introduction of the curable fluid composition into receptacle 18, the fluid composition is allowed to cure, for a time in the range of from about 5 seconds to about 5 minutes.

In some embodiments, wherein device 10 comprises at least one inlet, and the curable fluid composition comprises at least two components, each of the two components may be introduced through the same at least one inlet, either substantially simultaneously or sequentially. Alternatively, in embodiments wherein device 10 comprises at least two inlets, each of the two components may be introduced through a different, either substantially simultaneously or sequentially.

Following completion of the curing process, device 10 may be removed.

EXAMPLES

Materials and Methods:

Fibrin sealant used in the experiments below.

EVICEL® fibrin sealant (Omrix Biopharmaceuticals Ltd.) including a fibrinogen component (Biological Active Component 2; BAC2), and a thrombin component.

Burst pressure test.

The burst pressure provides an indication of the ability of a tested formulation to adhere to an organ tissue and maintain its mechanical integrity up to the pressure point in which a burst of the seal occurs, resulting in immediate loss of pressure and visible water leakage. The burst pressure test was carried out essentially as described in Vilela et al. ["What is Important For Continent Catheterizable Stomas: Angulations or Extension?" Int Braz J Urol. 2007; Vol. 33(2): 254-263] to determine and evaluate the ability of a tested formulation e.g. sealant to effectively seal the organ and withstand pressure.

Briefly, specially designed 2 aluminum pipes (having a conical shape on one end), each having a length of 9.5 cm and provided with holes, were inserted in the opposite sides of a tubular segment of a pig ileum (having a length of 25-30 cm and a diameter of about 3 cm). The pipes were inserted into the ileum segment from the opposite sides with the conical shape protruding out of the segment and by leaving a space of about 10 cm between the two pipes. The tubular segment was sealed at both ends by placing a plastic ring on the conical part of the pipe, when the intestine end is placed between the conical aluminum part and the plastic ring. The two plastic rings at both ends were tightened using metal screws.

A 5 mm incision was formed perpendicular to the ileum tissue length at the middle of the 10 cm space between the two pipes using a sharp blade, and the tissue was positioned with the incision faced down (to imitate the complexity of sealing leaks of 'hard to reach' organs). Following creation of the 5 mm incision, 4 ml fibrin sealant (an equal volume of both the fibrinogen and thrombin components) was applied onto the incision area in one of the different application methods specified below:

1—Dripping onto the upper side of the tissue at a distance of 3-4 cm from the target tissue using the EVICEL® applicator device without gas; the dripping rate was about 4 ml/minute. The entire volume of the components were dripped onto the upper side of the tissue and were allowed to flow onto the sides of the tissue;

2—Spraying onto the upper side of the tissue at 25 psi from a distance of 10 cm from the target tissue using the EVICEL® applicator device; the spraying rate was carried out at about 4 ml/minute. The entire volume of the components were sprayed to the upper side of the tissue and were allowed to flow onto the sides of the tissue; or 3—By using the device described herein. The tissue was placed on top of spaced-apart walls 16a and 16b substantially parallel to spaced-apart sides 14a and 14b (see FIG. 2). In this manner gaps 32a and 32b were formed as described above. The device was deployed beneath the tissue in such a manner that the incision was facing down and situated between spaced-apart sides 14a and 14b, allowing spaced-apart walls 16a and 16b to support the tissue at both sides.

Two ml sealant (equal volume of both components) was dripped without gas into gaps 32a and 32b at a rate of about 4 mi/minute by inserting the tip of EVICEL® applicator device into the gaps and allowing the sealant to accumulate in receptacle 18 (see FIGS. 1 and 2). In a next step, the remaining fibrin sealant volume (2 ml; equal volume of both components) was dripped onto the upper side of the tissue using the EVICEL® applicator device without gas at a rate of about 4 ml/minute and at a distance of 3-4 cm from the upper side of the tissue. The sprayed volume was allowed to flow onto the sides of the tissue.

In all three methods, application to the upper side of the tissue was carried out by moving the tip of the EVICEL® applicator back and forth and creating a 15 mm band [7.5 mm on each side of the incision (perpendicular to the incision)].

In all methods, the fibrin was left to cure at room temperature (about 20-25° C.) for 10 minutes. In method 3, the device was removed from underneath the tissue after the above curing step.

In the third method, when using the applicator according to the invention, the entire circumference of the intestine was covered by the sealant (a 15 mm band was created around the entire circumference).

In the burst pressure test, the two components were used in a 1:1 volume ratio, the final fibrinogen concentration applied was 30.5 mg/ml, and the final thrombin concentration applied was 584 IU/ml.

For the testing of the burst pressure, the intestine was pressurized by connecting one of the aluminum pipes to a water source while the other pipe remained sealed (to avoid flow of water through that pipe). Water was allowed to flow into the aluminum pipe inflating the intestine while monitoring the internal pressure. The water pressure increased until the seal of the incision burst, and a sharp drop in pressure was observed. The observed pressure level was continuously monitored using a pressure gauge (D-logmate 590 MRC Israel) which was connected to the liquid flow line. The maximum pressure achieved prior to the pressure drop was recorded and considered as the burst pressure. Typically, a higher burst pressure value indicates a greater sealing strength.

Example 1

Application of Fibrin Sealant Onto a Staple Line Using a Device as Described Herein In this example, a device according to the invention is used for application of fibrin sealant onto a staple line following a gastrointestinal anastomosis procedure in the lower part of the rectum. Fibrin sealant was applied around the entire circumference of the rectum, a challenging application due to the limited space around the organ.

Each of spaced-apart walls 16a and 16b has a length (marked as 20 in FIG. 1) of 6 cm. Each of spaced-apart sides 14a and 14b has a length (marked as 15 in FIG. 1) of 2 cm. A portion of length 20c of each of spaced-apart walls 16a and 16b has a height (marked as 25 in FIG. 1) of 5 mm above the upper face of lower surface 12, and a thickness of 2 mm (marked as 23 in FIG. 1). Spaced-apart sides 14a and 14b, and portions 20a and 20b of spaced-apart walls 16a and 16b have a height of 25 mm (marked as 17 in FIG. 1) and a thickness of 2 mm (marked as 19 in FIG. 1). Lower surface 12 has a thickness of 2 mm.

In some embodiments, the device s made of silicone. Alternatively, the device may be made of nylon, polyurethane, polyester, polychloroprene, or polytetrafluoroethylene (PTFE), or a combination thereof.

The anastomis procedure is carried out as described in Yik-Hong Ho et. al. ("Techniques for colorectal anastomosis", World J Gastroenterol. Apr. 7, 2010; 16(13):1610-21). The procedure includes removal of 10 cm of the rectum and stapling it with J&J, ECHELON FLEX™ ENDOPATH® stapler.

In the next step, device 10 (provided to the user in a sterile package) is deployed beneath the rectum by gently lifting the rectum and placing it on top of spaced-apart walls 16a and 16b, and substantially parallel to spaced-apart sides 14a and 14b (see FIG. 2). In this manner gaps 32a and 32b are formed as described above. Device 10 is deployed beneath the rectum in such a manner that the staple line is situated between spaced-apart sides 14a and 14b, allowing spaced-apart walls 16a and 16b to support the rectum at both sides of the staple line.

Following deployment of the device, 5 ml fibrin sealant (an equal volume of fibrinogen component and thrombin component of EVICEL®, Omrix biopharmaceuticals Ltd., Israel) is dripped through at least one of gap 32a, 32b using an applicator device as described in WO2007/059801 until receptacle 18 is filled with fibrin sealant.

Then, in order to get full coverage around the circumference of the rectum, an additional 5 ml fibrin sealant is dripped on top of the rectum.

After about 60 seconds, the fibrin cures and the device is removed from beneath the rectum leaving a continuous layer around the entire circumference of the rectum.

Example 2

Application of Fibrin Sealant onto an Incision Area by Using Different Methods

In the following experiment, the efficacy of a device according to the invention in 'applying fibrin sealant onto a circumference of a target area' was studied. The performance of EVICEL® following application by using the device of FIG. 1 was evaluated using the burst test described above. A device made of polyurethane and having the following dimensions was used:

Each of spaced-apart watts 16a and 16b has a length (marked as 20 in FIG. 1) of 4.3 cm. Each of spaced-apart sides 14a and 14b has a length (marked as 15 in FIG. 1) of 2 cm. A portion of length 20c of each of spaced-apart walls 16a and 16b has a height (marked as 25 in FIG. 1) of 2.5 mm above the upper face of lower surface 12, and a thickness of 2.5 mm (marked as 23 in FIG. 1). Spaced-apart sides 14a and 14b, and portions 20a and 20b of spaced-apart walls 16a and 16b have a height of 17 mm (marked as 17 in FIG. 1) and a thickness of 2 mm (marked as 19 in FIG. 1). Lower surface 12 has a thickness of 2 mm.

Spraying and dripping applications (Application method 1 and 2 as elaborated under the "Burst pressure test" in the Materials and Methods section) were used as reference. Six replicates for each treatment were carried out.

The results of the Burst Pressure Test for each application method are presented in Table 1 below.

TABLE 1

Burst pressure obtained following application of fibrin sealant in different application methods.

| | Burst pressure (mmHg) | | |
|---|---|---|---|
| | Application by dripping (Method 1) | Application by spraying (Method 2) | Application by using the device according to the invention (Method 3) |
| 1 | 22.50 | 14.25 | 50.25 |
| 2 | 7.50 | 8.25 | 102.01 |
| 3 | 19.50 | 4.50 | 69.01 |
| 4 | 16.50 | 5.25 | 84.76 |
| 5 | 21.00 | 20.25 | 78.76 |
| 6 | 12.75 | 15.75 | 39.75 |
| Average | 16.63 | 11.38 | 70.76 |
| Standard deviation | 5.66 | 6.34 | 72.90 |

It was observed that a higher pressure was needed in order to burst the fibrin seal on the intestine tissue when fibrin was applied with the device according to the invention, allowing to cover the entire circumference of the intestine in a uniform manner by enabling application of the sealant also to the lower portion of the tissue, as compared to the pressure needed to burst the fibrin seal when applied by either spraying or dripping.

These results indicate that using a device according to the invention to form a fibrin seal results in a greater adhesive force.

It was therefore concluded that the sealing strength when using the device according to the invention was superior as compared to the sealing strength obtained following application by dripping or spraying.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A device for application of a curable fluid composition on a staple line in a bodily organ, the device comprising:
   (i) a monolithic piece of material having a lower surface, two spaced-apart sides, and two spaced-apart walls connecting the two spaced-apart sides, wherein at least a first portion of each of the two spaced-apart walls, proximal to at least one of the two spaced-apart sides of the monolithic piece, has a height greater than that of a second portion of each of the two spaced-apart walls, wherein a receptacle for containing the curable fluid composition therein is defined by the lower surface, the two spaced-apart sides, and the two spaced-apart walls, wherein the monolithic piece is devoid of an opening at the lower surface, and wherein: each of the two spaced-apart sides has a length in the range of from about 1 cm to about 6 cm and a height in the range from about 5 to about 70 mm, wherein each of the two spaced-apart walls has a length in the range from 2 to 10 cm, wherein the monolithic piece is configured to be deployed underneath the bodily organ such that: a lower portion of the bodily organ is supported by at least a portion of each of the two spaced-apart walls, and at least one gap is created between a side of the bodily organ and the at least one side of the monolithic piece; and (ii) an applicator configured to introduce the curable fluid composition after deployment through the at least one gap.

2. The device of claim 1, wherein when the monolithic piece is deployed underneath the bodily organ such that the lower portion of the bodily organ is supported by the second portion of each of the two spaced-apart walls, the at least one gap is created between the side of the bodily organ and the at least one side of the monolithic piece.

3. The device of claim 2, wherein the portion of each of the two spaced-apart walls, proximal to each of the two spaced-apart sides, has a height greater than that of the second portion of each of the two spaced-apart walls, wherein when the monolithic piece is deployed underneath the bodily organ such that the lower portion of the bodily organ is supported by the second portion of each of the two spaced-apart walls, the at least one gap is created between each side of the bodily organ and each side of the monolithic piece.

4. The device of claim 1, wherein the monolithic piece is made of a rigid or semi-rigid material.

5. The device of claim 1, wherein each of the two spaced-apart sides has a thickness in the range from about 1 to about 15 mm.

6. The device of claim 1, wherein each of the two spaced-apart walls has a thickness in the range from about 1 to about 15 mm.

7. The device of claim 1, wherein at least a portion of each of the two spaced-apart walls has a height in the range from about 2 to about 15 mm.

8. The device of claim 1, wherein the lower surface has a thickness in the range from about 0.5 to about 10 mm.

* * * * *